(12) United States Patent
Mills et al.

(10) Patent No.: US 11,686,731 B2
(45) Date of Patent: Jun. 27, 2023

(54) PROSTATE CANCER MARKERS AND USES THEREOF

(71) Applicants: Ian Mills, Belfast (GB); Ingrid Jenny Guldvik, Oslo (NO)

(72) Inventors: Ian Mills, Belfast (GB); Ingrid Jenny Guldvik, Oslo (NO)

( * ) Notice: Subject to any disclaimer, the term of this patent is extended or adjusted under 35 U.S.C. 154(b) by 700 days.

(21) Appl. No.: 15/540,295

(22) PCT Filed: Jan. 5, 2016

(86) PCT No.: PCT/IB2016/000085
§ 371 (c)(1),
(2) Date: Jun. 28, 2017

(87) PCT Pub. No.: WO2016/110782
PCT Pub. Date: Jul. 14, 2016

(65) Prior Publication Data
US 2018/0267044 A1    Sep. 20, 2018

Related U.S. Application Data

(60) Provisional application No. 62/099,837, filed on Jan. 5, 2015.

(51) Int. Cl.
*G01N 33/574* (2006.01)

(52) U.S. Cl.
CPC . *G01N 33/57434* (2013.01); *G01N 2333/475* (2013.01); *G01N 2333/4728* (2013.01); *G01N 2333/96425* (2013.01); *G01N 2800/52* (2013.01)

(58) Field of Classification Search
CPC .. G01N 33/53; G01N 33/574; G01N 2800/00; G01N 2800/52; G01N 2800/54; G01N 2800/56
See application file for complete search history.

(56) References Cited

U.S. PATENT DOCUMENTS

| | | | |
|---|---|---|---|
| 8,790,647 | B2 | 7/2014 | Greenwood |
| 2013/0084276 | A1 | 4/2013 | Watson et al. |
| 2013/0102011 | A1 | 4/2013 | Zhou et al. |
| 2013/0323751 | A1 | 12/2013 | Singbartl et al. |
| 2014/0121127 | A1 | 5/2014 | Speicher |
| 2014/0271621 | A1 | 9/2014 | Hemken |
| 2014/0377277 | A1 | 12/2014 | Greenwood |
| 2015/0132226 | A1 | 5/2015 | Greenwood |
| 2015/0141273 | A1 | 5/2015 | Bosch |
| 2016/0109437 | A1 | 4/2016 | Cooper |

FOREIGN PATENT DOCUMENTS

| | | |
|---|---|---|
| CN | 102243240 | 11/2011 |
| CN | 103487493 | 1/2014 |
| WO | WO2011027129 | 3/2011 |
| WO | WO2011092219 | 8/2011 |
| WO | WO2012102963 | 8/2012 |
| WO | WO2013033019 | 3/2013 |
| WO | WO2013132267 | 9/2013 |
| WO | 2013/152989 | 10/2013 |
| WO | WO2013152989 | 10/2013 |
| WO | WO2015006515 | 1/2015 |
| WO | WO-2015092046 A2 * 6/2015 ....... G01N 33/57434 |  |

OTHER PUBLICATIONS

Bolla et al., Lancet, 2002, 360:103-108.*
Fan et al., J. Proteome Res, 2011, 10: 1361-1373.*
International Search Report & Written Opinion, International Patent Application No. PCT/IB2016/000085, dated Mar. 30, 2016.
Anonymous "Lecture by Ingrid Jenny Guldvik, MSc (Mills Group, NCMM)—For employees—University of Olso" Nov. 16, 2015, Retrieved from the Internet: www.uio.no/english/for-employees/unitpages/med/biotek/events/Tuesday-seminar/lectures/ingrid_april2015.html [retrieved on Mar. 16, 2016] abstract.
Thomasson, M. et al. LRIGI and the liar paradox in prostate cancer: a study of the expression and clinical significance of LR1G1 in prostate cancer International Journal of Cancer, 128: 2843-2852 (2011).
Brown et al., "Macrophage Inhibitory Cytokine 1: A New Prognostic Marker in Prostate Cancer" Clin Cancer Res. 2009, 15(21):6658-64.
Cummings et al., "Serum leucine-rich alpha-2-glycoprotein-1 binds cytochrome c and inhibits antibody detection of this apoptotic marker in enzyme-linked immunosorbent assay." Apoptosis 2006, 11(7):1121-9.
Kobe et al., "The leucine-rich repeat as a protein recognition motif." Curr Opin Struct Biol 2001, 11(6):725-32.
Linden, M. et al. "Tumour expression of bladder cancer-associated urinary proteins" BJU International, 2013, 112, 407-415.
Liu "Letter to the Editor: Shotgun and targeted proteomics reveal that pre-surgery serum levels of LRG1, SAA, and C4BP may refin prognosis of resected squamous cell lung cancer" Journal of Molecular Cell Biology, 2012, 4, 344-347.
O'Donnell et al., "Molecular characterization and expression analysis of leucine-rich alpha2-glycoprotein, a novel marker of granulocytic differentiation." J Leukocyte Biol 2002, 72(3):478-85.
Office Action, U.S. Appl. No. 13/618,005, dated Sep. 30, 2013.
Saito et al., Gene Expression Profiling of Mucosal Addressin Cell Adhesion Molecule-1+ High Endothelial Venule Cells (HEV) . . . J Immunol 2002, 168(3):1050-9.
Sun et al., Differentially expressed genes in TGF-Beta1 sensitive and resistant human hepatoma cells, Cancer Lett 1995, 89(1):73-9.

(Continued)

*Primary Examiner* — Hong Sang
(74) *Attorney, Agent, or Firm* — Casimir Jones S.C.; J. Mitchell Jones

(57) ABSTRACT

The present invention relates to compositions and methods for cancer diagnosis, research and therapy, including but not limited to, cancer markers. In particular, the present invention relates to LRG1 protein markers for use in the diagnosis, prognosis, and determination of treatment of prostate cancer.

9 Claims, 8 Drawing Sheets

(56) References Cited

OTHER PUBLICATIONS

Takahashi et al., "Periodicity of leucine and tandem repetition of a 24-amino acid segment in the primary structure of leucine-rich alpha 2-glycoprotein of human serum." Proc Natl Acad Sci U S A 1985, 82(7):1906-10.
Wang et al. "LRG1 expression indicates unfavorable clinical outcome in hepatocellular carcinoma" Oncotarget, vol. 6, No. 39, 2015, pp. 42118-42129.
Wen et al. "LRG1 is an independent prognostic factor for endometrial carcinoma" Tumor Biol. 2014 35:7125-7133.
Written Opinion of the International Preliminary Examining Authority, International Patent Application No. PCT/IB2016/00085, dated Sep. 16, 2016.

\* cited by examiner

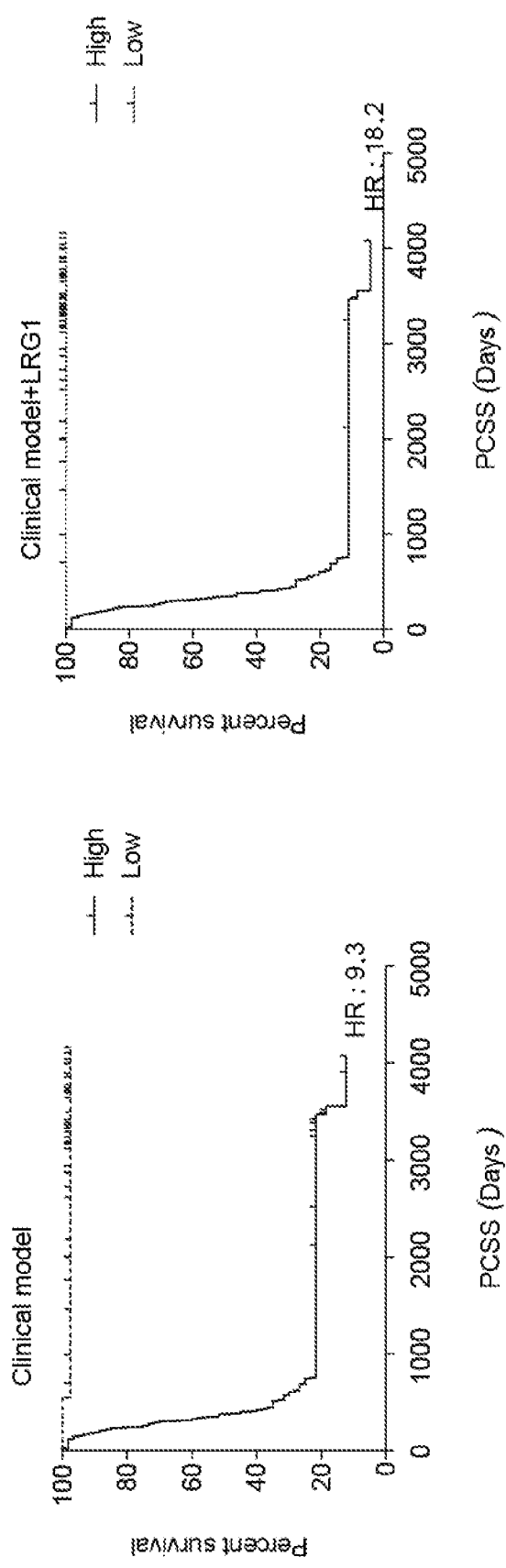

PROSTATE CANCER MARKERS AND USES THEREOF

CROSS REFERENCE TO RELATED APPLICATIONS

The present invention is a U.S. 371 national phase entry of International Patent Application No. PCT/IB2016/000085, international filing date Jan. 5, 2016, which claims the priority benefit of U.S. Provisional Patent Application 62/099,837, filed Jan. 5, 2015, the contents of which are incorporated by reference in their entireties.

FIELD OF THE INVENTION

The present invention relates to compositions and methods for cancer diagnosis, research and therapy, including but not limited to, cancer markers. In particular, the present invention relates to LRG1 protein markers for use in the diagnosis, prognosis, and determination of treatment of prostate cancer.

BACKGROUND OF THE INVENTION

Prostate cancer is the commonest non-epithelial cancer in men in Norway, much of Western Europe and the USA. Approximately 9 million new cases are diagnosed worldwide annually and approximately 260,000 deaths occur due to prostate cancer, positioning it as the sixth leading cause of cancer-associated deaths. In men it represents the third most common cause of cancer-associated fatality after lung and colorectal cancer. Incidence in men under the age of 50 is rare and often associated strongly with family history and genetic predisposition. The incidence rises significantly with age and ethnicity has also been reported to be a significant risk factor in cohort studies. The five-year survival rate for localized disease is 100% however upon progression the survival rate drops to <50%.

Owing to the high-incidence of prostate cancer together with the prolonged time to progression (5-10 years) occurring in a minority of detected cases (~20%), there is a pressing need for improved early detection and more robust risk stratification at the time of diagnosis. This is important to ensure that precious clinical resources are targeted as effectively as possible on those that will benefit most from primary treatment (surgery or radiotherapy) and may also benefit from the most intensive post-treatment follow-up and where necessary additional treatment upon recurrence (e.g., anti-androgens, androgen synthesis inhibitors, chemotherapy, beamline radiotherapy).

The optimal test for prostate cancer represents a panel of biomarkers with considerable specificity for prostate cancer combined with biomarkers predictive of metastatic progression and perhaps shared across cancer types due to conservation of biological process. A number of prostate-specific biomarkers have been reported. The earliest to be adopted clinically was prostate-specific antigen (PSA) which is now a mainstay as a blood test however because this marker is also expressed basally by non-cancerous prostate tissue its effective implementation requires the establishment of baseline levels for individuals, repeat testing and careful attention to decision thresholds (Green et al, J Urol. 2013 January; 189(1 Suppl):S2-S11). Nonetheless, it is now often the gatekeeper test to needle biopsy and pathology grading (Gleason score) and staging of the disease. Subsequently other prostate cancer-specific biomarkers have been proposed to augment PSA testing and often are positioned to enhance the probability of identifying cancer on repeat biopsy. The markers that have advanced furthest in this setting are detected using PCR-based assays and are PCA3 (Gittelman et al, J Urol. 2013 July; 190(1):64-9) and the TMPRSS2-ERG gene fusion (Yao et al, Tumour Biol. 2014 March; 35(3):2157-66). The former is now clinically approved in the USA. By contrast, no progress has so far been made in adopting biomarkers for upfront prognostication into the clinical routine. This is despite the fact that in the absence of such markers there is a significant probability of expensive overtreatment of the disease in some settings due to its high incidence.

Additional markers for providing prostate cancer prognoses are needed.

SUMMARY OF THE INVENTION

The present invention relates to compositions and methods for cancer diagnosis, research and therapy, including but not limited to, cancer markers. In particular, the present invention relates to LRG1 protein markers for use in the diagnosis, prognosis, and determination of treatment of prostate cancer.

For example, in some embodiments, the present invention provides a method for providing a prognosis for a subject with prostate cancer, or selecting a subject with prostate cancer for treatment with a particular therapy, comprising: (a) detecting the level of LRG1 polypeptide in a sample from the subject using an in vitro assay and (b) comparing the level of the LRG1 polypeptide to a reference level of LRG1 polypeptide (e.g., the level in a subject not diagnosed with prostate cancer, the level in a subject with localized prostate cancer, the level in a subject with indolent prostate cancer or another relevant control), wherein an altered amount of the LRG1 polypeptide relative to said reference provides an indication selected from, for example, an indication of survival of the subject or an indication that the subject is a candidate for treatment with a particular therapy or that the subject is likely to respond favorably to treatment with a particular therapy, e.g., androgen deprivation therapy in combination with radiotherapy. In some embodiments, elevated amounts of the LRG1 polypeptide in the biological sample as compared to the reference level are indicative of a decreased likelihood of survival of the subject. In some embodiments, elevated amounts of the LRG1 polypeptide in the biological sample as compared to the reference level are indicative of an increased likelihood of disease recurrence in the subject following treatment with surgery or radiotherapy. In some embodiments, elevated amounts of said LRG1 polypeptide in the biological sample as compared to the reference level are indicative that the subject is a candidate for more aggressive adjuvant therapy. In some embodiments, elevated amounts of said LRG1 polypeptide in the biological sample as compared to the reference level are indicative that the subject is a candidate for treatment with a combination of androgen deprivation therapy in combination with radiotherapy. In some embodiments, the in vitro assay is an immunoassay. In some embodiments, the sample comprises, for example, bone marrow, a prostate cancer cell, blood, serum, plasma, urine, prostatic fluid or semen. In some embodiments, the detecting comprises contacting the sample with reagents (e.g., an antibody that specifically binds to LRG1) that specifically bind to LRG1. In some embodiments, the expression level (e.g., nucleic acid or polypeptide levels) of one or more additional prostate cancer markers is determined in combination with LRG1 (e.g., one or more of PSA and GDF15/MIC-2 (Brown et al, Clin Cancer Res. 2009, 15(21):6658-64), and/or other prostate specific markers). In some embodiments, the subject has undergone surgery and/or radiotherapy and elevated amounts of LRG1 polypeptide in the biological sample as compared to the reference level is indicative that the subject is at an increased risk of prostate-specific death after surgery and/or radiotherapy. In some embodiments, the subject has or is undergoing combined radiotherapy and androgen-deprivation therapy and elevated amounts of LRG1 polypeptide in the bone marrow of the subject is indicative of increased risk of recurrence of prostate cancer and/or survival in the subject.

Further embodiments provide the use of a reagent that specifically detects elevated level of LRG1 polypeptide in a sample from a subject in the determination of the likelihood of survival of the subject, increased risk of recurrence of prostate cancer in the subject, or determining that the subject is a candidate for treatment with a particular therapy.

Yet other embodiments provide a kit and/or system for detecting the level of LRG1 polypeptide in a sample from a subject, comprising: a) a reagent that specifically detects a LRG1 polypeptide: and b) a reference standard; and optionally computer software and a computer processor configured to provide an indication selected from an indication of survival of the subject, increased risk of recurrence of prostate cancer in the subject, or an indication that the subject is a candidate for treatment with a particular therapy.

Additional embodiments are described herein.

DESCRIPTION OF THE FIGURES

FIG. 3A-B shows that LRG1 improves the clinical model for risk stratification of prostate cancer patients. High-risk group was defined at a cut off of 10% probability of prostate cancer specific mortality. A) A clinical model with age, PSA, biopsy Gleason score and T stage. B) The clinical model is supplemented with LRG1 plasma concentrations.

DEFINITIONS

Figure 1A:
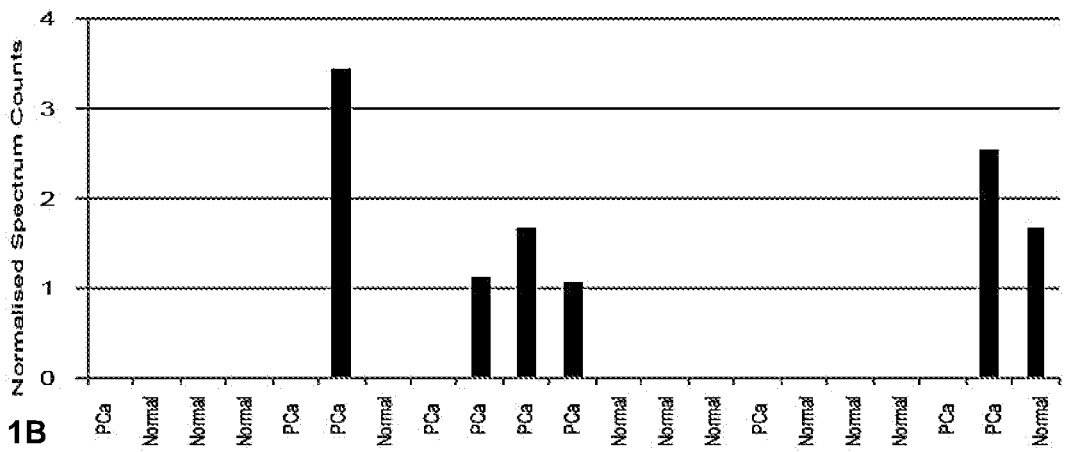
FIG. 1A-D shows LRG1 concentrations in Janus Serum samples. A) Normalized spectrum counts for LRG1 in serum samples. B) Western blot validation of LRG1 levels in depleted serum samples. C) ELISA measurements of LRG1 in full serum from 31 men without prostate cancer diagnosis at time of blood-draw versus 30 men with prostate cancer detected. D) ROC analysis of LRG1 concentrations in serum samples.

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., murines, simians, equines, bovines, porcines, canines, felines, and the like), and most preferably includes humans.

The term "diagnosed," as used herein, refers to the recognition of a disease by its signs and symptoms, or genetic analysis, pathological analysis, histological analysis, and the like.

A "subject suspected of having cancer" encompasses an individual who has received an initial diagnosis (e.g., a CT scan showing a mass or increased PSA level) but for whom the stage of cancer or presence or absence of LRG1 polypeptide levels indicative of cancer prognosis is not known. The term further includes people who once had cancer (e.g., an individual in remission). In some embodiments, "subjects" are control subjects that are suspected of having cancer or diagnosed with cancer.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of LRG1 polypeptide levels in cancer cells.

As used herein, the term "characterizing a prostate sample in a subject" refers to the identification of one or more properties of a prostate tissue sample (e.g., including but not limited to, the presence of cancerous tissue, the level of LRG1 polypeptide, the presence of pre-cancerous tissue that is likely to become cancerous, and the presence of cancerous tissue that is likely to metastasize, the presence of cancerous tissue that is likely to recur, or othe likelihood of prostate cancer specific death). In some embodiments, tissues are characterized by the identification of the level of LRG1 polypeptide.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "purified" or "to purify" refers to the removal of components (e.g., contaminants) from a sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, and tissues. Biological samples include blood products, such as plasma, serum and the like. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, the present invention relates to LRG1 protein markers for use in the diagnosis, prognosis, and determination of treatment of prostate cancer.

Prostate cancer is a high-incidence male cancer with a significant age association and progression in a subset of diagnosed cases. In the absence of effective prognostication there are significant social and economic costs associated with overtreatment and unnecessary treatment. Improved upfront risk stratification would transform healthcare delivery and alleviate stresses on families, patients and medical practitioners.

Experiments performed during development of embodiments of the present invention utilized sample collections and follow-up data to identify a blood-based prognostic protein biomarker, LRG1, which is detectable using a cheap and commercially available ELISA assay. It was shown that LRG1 is associated with high-stage, high-grade and ultimately fatal prostate cancers if elevated in samples drawn at diagnosis. Specifically, it was shown that elevated levels of LRG1 in blood was associated with poorer outcome of both surgery and radiotherapy treatment. This indicates that such subjects are candidates for more aggressive adjuvant therapy. It was further shown that patients with high LRG1 benefit significantly from treatment with androgen deprivation therapy combined with radiotherapy versus androgen deprivation therapy alone. Finally, it was shown that LRG1 levels in bone marrow is associated with outcome (both disease recurrence and overall survival) in patients treated with androgen deprivation therapy combined with radiotherapy. LRG1 represents a unique example of a blood-based prostate cancer biomarker able to both enhance risk stratification and treatment decision-making. LRG1 is a TGF beta-receptor superfamily ligand implicated in angiogenesis and endothelial development.

For example, in some embodiments, the present invention provides compositions and methods for detecting LRG1 polypeptide levels for use in providing a prognosis or determining a treatment course of action or predicting a response to treatment in a subject diagnosed with prostate cancer or undergoing treatment for prostate cancer.

In some embodiments, LRG1 polypeptide levels are detected in combination with one or more additional prostate cancer markers (e.g., PSA and/or GDF15/MIC-1). Additional suitable markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); RAS/KRAS (Bos, Cancer Res. 49:4682-89 (1989); Kranenburg, Biochimica et Biophysica Acta 1756:81-82 (2005)); and, those disclosed in U.S. Pat. Nos. 5,854,206 and 6,034,218, 7,229,774, each of which is herein incorporated by reference in its entirety. Markers for other cancers, diseases, infections, and metabolic conditions are also contemplated for inclusion in a multiplex or panel format.

The present invention is not limited to a particular polypeptide detection method. Any suitable method may be utilized. In some embodiments, immunoassays are utilized.

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Antibodies useful in assays for detecting LRG1 may be any monoclonal or polyclonal antibody, as long as it can recognize, preferably specifically, LRG1.

Embodiments of the present invention further provide kits and systems comprising reagents for detection of LRG1 levels or present in samples (e.g., antibodies). In some embodiments, kits and systems comprise computer systems for analyzing LRG1 levels and providing diagnoses, prognoses, or determining treatment courses of action.

In some embodiments, a computer-based analysis program is used to translate the raw data generated by the detection assay (e.g., level of LRG1 polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced (i.e., LRG1 polypeptide levels) specific for the diagnostic or prognostic information desired for the subject.

The profile data is then prepared in a format suitable for interpretation by a treating clinician. For example, rather than providing raw data, the prepared format may represent a diagnosis or risk assessment (e.g., level of LRG1 polypeptide) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

The compositions, kits, systems, uses, and methods described herein find use in the diagnosis and prognosis of prostate cancer, as well as in determining a treatment course of action for a subject diagnosed with prostate cancer. For example, in some embodiments, compositions and method described herein are used to provide a prognosis of one or more of risk of prostate cancer recurrence, risk of prostate cancer metastasis, and/or risk of prostate cancer specific death. In some embodiments, such prognoses, along with LRG1 levels, are used to determine a treatment course of action in a subject diagnosed with prostate cancer (e.g., use of adjunct radiotherapy and/or androgen depletion therapy, or watchful waiting). In some embodiments, LRG1 levels (e.g., in a prostate cancer biopsy, urine sample, blood sample, or bone marrow sample) are tested one or more times before, during, or after prostate cancer treatment. In some embodiments, LRG1 levels are used to alter a prostate cancer treatment course of action (e.g., stop, start, or change a treatment).

EXPERIMENTAL

The following examples are provided in order to demonstrate and further illustrate certain preferred embodiments and aspects of the present invention and are not to be construed as limiting the scope thereof.

Example 1

Methods
Patient Samples
Janus Serum Bank
The Janus Serum Bank (owned by the Cancer Registry of Norway) was established in 1972 for retrospective epidemiological studies on health and disease within Norway. Blood samples were obtained from 61 nonfasting participants, serum was separated following standard methods, and all samples were stored at −25° C. The samples went through two thaw-freeze cycle for preparation of aliquots for the present study. Within the 61 blood samples, 31 samples were collected from men without prostate cancer diagnosis at time of blood draw and 30 samples were collected post prostate cancer diagnosis. Within these, 40 samples were nested controls, with matched pre- and post-diagnosis sampling.

STHLM2

The STHLM2 cohort consist of men referred for PSA testing in laboratories connected to the Karolinska University Laboratory and Alerts Medilab in Stockholm County, Sweden, between Nov. 1, 2010, and Sep. 1, 2012. Whole blood were collected in ethylenediaminetetraacetic acid tubes without gel and plasma was separated by centrifugation, aliquoted and stored at −80° C. until analysis. Plasma samples from 764 participants were obtained from the Karolinska Biobank for analysis. Of the 669 participants with complete clinical data, 296 with no cancer detected and 373 with prostate cancer at time of blood draw.

Cancer of Prostate Sweden

CAncer Prostate in Sweden (CAPS) is a population-based study with participants enrolled between March 2001 and October 2003. Plasma samples from 200 participants were drawn from Biobanken Non, Västrebotten, Sweden, carefully selected to represent four groups; 50 control (cancer-free during 10 years of follow-up), 50 pre-diagnosis (cancer within 10 years), 50 localized cancer (no progression), 50 aggressive (prostate cancer-specific mortality within 10 years of diagnosis).

SPCG7

Scandinavian Prostate Cancer Group Study 7 (SPCG-7) is an open, randomized phase III study for comparing endocrine therapy with and without local radiotherapy, followed by castration on progression. Patient criteria for enrollment were age less than 76, life expectancy more than 10 years, locally advanced prostate cancer (T1b-T2 or T3), PSA less than 70 ng/mL and no evidence of metastasis.

Abundant Serum Protein Depletion

In order to reduce the dynamic range of proteins in full serum and thereby increase the detection limit for proteins of low abundance, ProteoSpin™ Abundant Serum Depletion Kit (Norgen Biotek, 17300) was used. This kit is based on the removal of the most abundant proteins found in serum, e.g albumins, transferrin, haptoglobulin and alpha-antitrypsin, by an ion-exchange column. Briefly, full serum was diluted in $dH_2O$ for the final concentration of 30 µg/µL as measured by NanoDrop 1000 (Thermo Scientific). Ten microliter of pre-diluted serum sample were then mixed with 490 µL Column Activator Buffer, and added to an activated ion-exchange column. The bound proteins in the column were washed twice prior to the elution step. The protein eluate, now depleted of abundant serum proteins, were neutralized, aliquoted and stored at −80° C. for downstream applications.

NanoLC-LTQ Orbitrap Mass Spectrometry

Two and a half microgram of depleted serum were subjected for mass spectrometry. Proteins were digested by in-solution trypsin digest. Peptides were analyzed by a ESI-Orbitrap (LTQ Orbitrap XL, Thermo Scientific, Bremen, Germany) mass spectrometer coupled to a nano-LC system. Peptides were purified by $C_{18}$ ZipTips (Millipore, Billerica, Mass., USA) prior to injection into an Ultimate 3000 nanoLC system (Dionex, Sunnyvale Calif.). For separation of peptides an Acclaim PepMap 100 column (50 cm×75 µm) packed with 100 Å C18 3 µm particles (Dionex) was used. A flow rate of 300 nL/min was employed with a solvent gradient of 7-35% B in 77 min, to 50% B in 10 min and then to 80% B in 2 min. Solvent A was 0.1% formic acid and solvent B was 0.1% formic acid/90% ACN. The mass spectrometer was operated in the data-dependent mode to automatically switch between Orbitrap-MS and LTQ-MS/MS acquisition. Survey full scan MS spectra (from m/z 300 to 2000) were acquired in the Orbitrap with the resolution R=60 000 at m/z 400 (after accumulation to a target of 500 000 charges in the LTQ). The method used allowed sequential isolation of the most intense ions, up to six, depending on signal intensity, for fragmentation on the linear ion trap using collision induced dissociation (CID) at a target value of 10 000 charges. For accurate mass measurements, the lock mass option was enabled in MS mode and the polydimethylcyclosiloxane ions generated in the electrospray process from ambient air were used for internal recalibration during the analysis. Target ions already selected for MS/MS were dynamically excluded for 60 sec. General mass spectrometry conditions were electrospray voltage, 1.6 kV; no sheath and auxiliary gas flow. Ion selection threshold was 5 000 counts for MS/MS and an activation Q-value of 0.25 and activation time of 30 ms were in addition applied for MS/MS. Data were acquired using Xcalibur v2.5.5 and processed using Proteome Discoverer v1.0 or Scaffold v.3.5.2.

Database Searching

Tandem mass spectra were extracted by [unknown] version [unknown]. Charge state deconvolution and deisotoping were not performed. All MS/MS samples were analyzed using Mascot (Matrix Science, London, UK; version 2.3.02). Mascot was set up to search the SwissProt_2011_11_database (selected for *Homo sapiens*, unknown version, 20252 entries) assuming the digestion enzyme trypsin. Mascot was searched with a fragment ion mass tolerance of 0.60 Da and a parent ion tolerance of 10.0 PPM. Ammonia-loss of the n-terminus, deamidated of asparagine and glutamine, oxidation of methionine, acetyl of the n-terminus and propionamide of cysteine were specified in Mascot as variable modifications. Scaffold (version Scaffold 3.6.5, Proteome Software Inc., Portland, Oreg.) was used to validate MS/MS based peptide and protein identifications. Peptide identifications were accepted if they could be established at greater than 95.0% probability as specified by the Peptide Prophet algorithm (Keller, A et al Anal. Chem. 2002; 74(20):5383-92). Protein identifications were accepted if they could be established at greater than 95.0% probability and contained at least 2 identified peptides. Protein probabilities were assigned by the Protein Prophet algorithm (Nesvizhskii, AI Anal Chem. 2003 Sep. 1; 75(17): 4646-58). Proteins that contained similar peptides and could not be differentiated based on MS/MS analysis alone were grouped to satisfy the principles of parsimony.

Western Blotting

Concentration of the protein elutes/depleted serum were determined by the BCA assay (Pierce) and equalized with neutralized elution buffer. Extracts were mixed with LDS NUPAGE sample buffer with reducing agent (Invitrogen) and incubated for 10 min at 70° C. Equal amounts of extracts (1.5 µg protein per lane) were loaded onto Criterion 4-20% gradient 26-well Tris-HCl gels (Bio-Rad) and wet-blotted (48 mM Tris, 39 mM Glycine, 0.02% SDS, 20% MeOH) to activated 0.45 µm PVDF membranes (Millipore) for 90 min at 55V under cooled conditions using Criterion blotter with plate electrodes (Bio-Rad). Even transfer and protein loading was confirmed by Ponceau S staining (Sigma, P7170), which was removed by 0.1 M NaOH. Membrane were blocked for 45 min in 7.5% nonfat milk (Cell Signaling Technology) in TBS-Tween (0.05%) followed by incubation with primary antibody recognizing LRG1 (Sigma, HPA001888), in 5% BSA/TBS-Tween (0.05%) over night at 4° C. Membrane was washed three times 10 minutes in TBS-Tween (0.05%) followed by 1 hour incubation with anti-rabbit-HRP (Dako, P0448) in a 1:2000 dilution in 5% BSA/TBS-Tween (0.05%). Bands were visualized with Novex® ECL Chemiluminescent Substrate Reagent (Invitrogen, WP20005) and detected with Hyperfilm (GE Healthcare) and developer (AGFA Curix-60). Bands were quantified using the Image J software (Bio-Rad, version 4.6.5).

LRG1 ELISA

The levels of LRG1 in serum/plasma samples were measured in duplicates using a commercially available solid-phase sandwich ELISA kit (IBL International GmbH, Hamburg, Germany). This assay has a sensitivity of 1.56 ng/ml to 100 ng/ml. The average intra-assay CV was 4.4% between the replicates, ranging 0.36-11.28. The concentrations of LRG1 in the serum/plasma samples were calculated by a four parametric curve-fit analysis of the standard curve (Excel).

Statistical Analysis

All statistical analyses were performed using SPSS v20 (Chicago, Ill., USA) package or Prism 5.0 (GraphPad) software. All patients missing clinical data on T stage, Gleason score and PSA were excluded from analysis. Kruskal-Wallis t-test was performed to evaluate significance ($p<0.05$) between groups. Logistic regression was performed with on log-transformed age, PSA and LRG1 values whereas T stage, Gleason score and risk categories defined by the National Institute for health and Care Excellence (NICE) was included as categorical variables (CG175: low risk Gleason score (GS) 2-6, PSA<10 ng/mL, Tumor stage (T) 1-2a, intermediate risk GS 7, PSA 10-20 ng/mL, T2b, and high risk GS8-10, PSA>20 ng/mL and T≥2c). Probability scores were used to assess the discriminatory power of the combined variables by receiver operating characteristic (ROC) curve analysis where the area under the curves (AUC) defined the discriminatory power. Prediction rule for metastatic lesions was elucidated from STHLM2 data and tested on the CAPS samples. Discriminatory power was assessed by ROC analysis. Decision curve analysis was performed to define optimal cut-off for the added value of LRG1 in risk stratification for prostate cancer specific mortality as assessed by Kaplan-Meyer.

Results

Figure 1B:
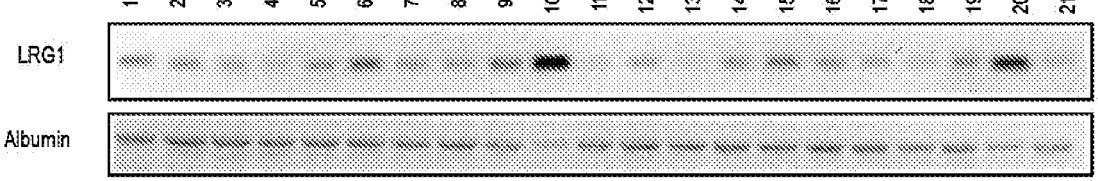
Figure 1C:
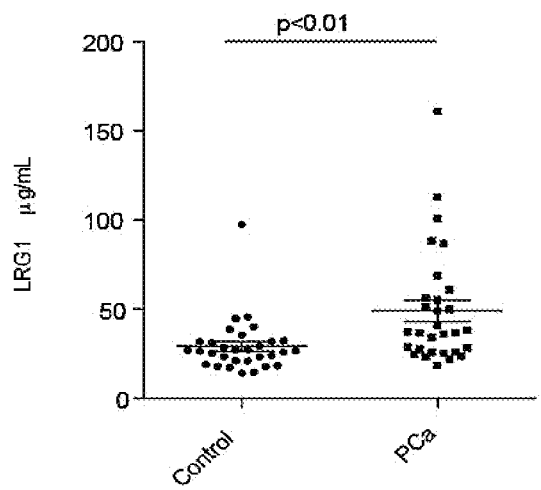
Figure 1D:
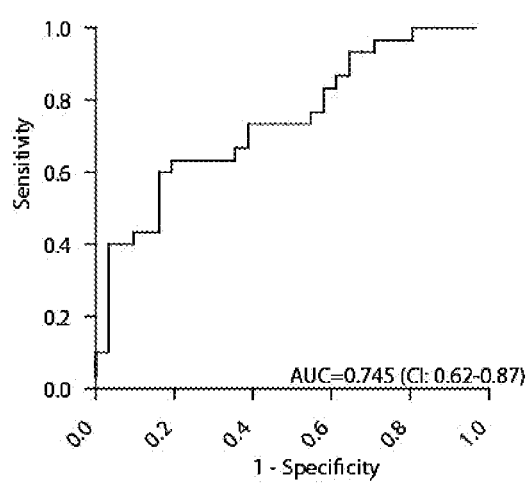

Scandinavia is one of the few regions in the world with a sufficiently integrated public health system, biobanking and cancer registries to support this work. In this study, three cohorts were used to identify prognostic biomarkers in blood samples. For clinical adoption biomarkers detectable in biological fluids represent are optimal for minimally invasive testing. In this study, the discovery cohort was samples from the Janus Serum Bank, a prospective population-wide serum bank containing multiple samples collected over time from a large number of individuals and linked to outcomes through the Norwegian Cancer Registry. Sixty one samples representing pre- and post-PCa diagnosis were used. A subset of these samples was processed to extract protein using a kit to deplete highly abundant serum albumins. Protein extracts were then run on an LC MS/MS instrument and the data were stratified based on peptide detection in the post-diagnosis versus pre-diagnosis cases with an emphasis on peptide counts and proteins identified solely in the post-diagnosis samples (FIG. 1A). Candidate proteins were then selected for further validation based on the availability of validated antibodies and literature reports linking candidates to cancers (FIG. 1B). LRG1 was prioritised because whilst it has been reported previously to be associated with poor prognosis in endometrial, colorectal and lung cancers no studies had previously evaluated it as a prostate cancer biomarker or linked it to prostate cancer. To assess it further, a commercially available ELISA kit was used to profile all of the Janus Serum Bank samples obtaining a statistically significant discrimination between pre- and post-diagnosis cases with high levels detected in those post-diagnosis cases in which peptide counts were discernible by mass spectroscopy (FIG. 1C, D). Having confirmed the utility of the ELISA for LRG1 detection in these serum samples, samples were obtained from two additional cohorts with associated detailed clinical data and follow-up. The first of these was the STHLM2 cohort, which is prospective population-wide cohort for whom the entry requirements were that individuals should be over the age of 60 and resident in Stockholm/Gotland. Recruitment to this cohort commenced in 2010 and the samples date from 2012. The samples in this case were plasma samples and owing to the limited follow-up time there was no data available on cause-of-death. However the cohort did have clinical data on cancer grade, stage and metastatic status as well as PSA measurements and age. In total, 764 samples were used. LRG1 expression was evaluated against all of these parameters. LRG1 improved prediction of high grade, high stage disease and metastatic/node positive cancers (Table 3). Given the indication that LRG1 may be more significantly associated with aggressive disease than prostate cancer as a whole, access to an additional cohort with much longer follow-up time was obtained. This second cohort, CAPS (Prostate Cancer of Sweden), used PSA measurements as an entry point to biopsy. Two hundred plasma samples with a minimum follow-up period post-PSA of 10 years were obtained. These were subdivided into 4 groups, 50 samples per group, consisting of:

Controls (n=50): No cancer detected during 10 years follow-up.

Pre-diagnosis (n=50): PCa detected within 10 years follow-up.

Localized PCa (n=50): indolent cancer at time of sampling, with no progression during 10 years of follow-up.

Aggressive PCa (n=50): PCa related death within 10 years of sampling date.

Figure 2:
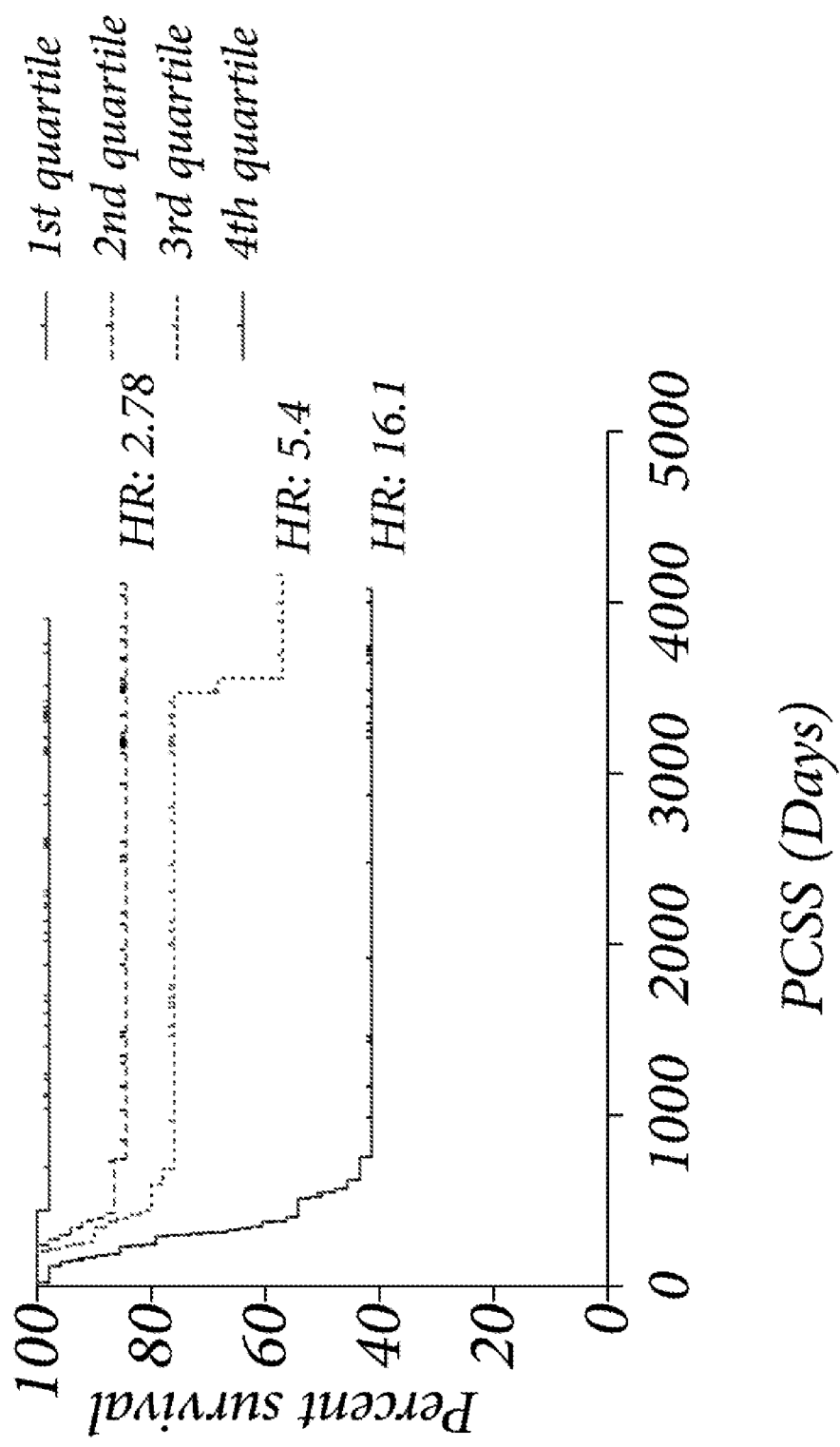
FIG. 2 shows LRG1 concentration defines risk for prostate cancer specific mortality. Kaplan Meyer survival analysis of patients grouped into 4 groups based on LRG1 concentrations (1st quartile represent the group with lowest LRG1 concentration, 4th quartile defines the group with highest LRG1 concentration).
Figure 4A:
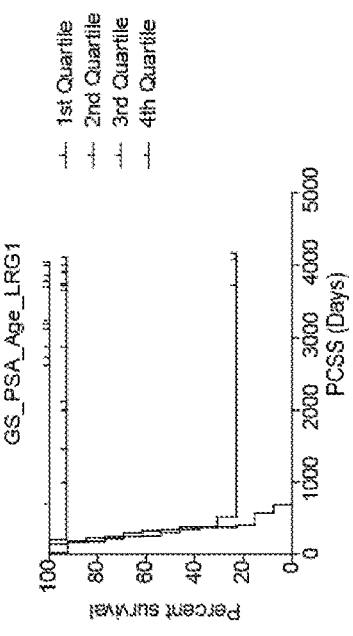
FIG. 4A-C shows that LRG1 improves a clinical model including GDF-15 for risk stratification of prostate cancer patients. Kaplan Meyer survival analysis of patients grouped into 4 groups based on predicted probability for prostate cancer specific mortality. A) A clinical model with age, PSA, biopsy Gleason score and GDF-15. B) The clinical model is supplemented with LRG1 plasma concentrations. C) The clinical model with LRG1 replacing GDF-15.
Figure 4B:
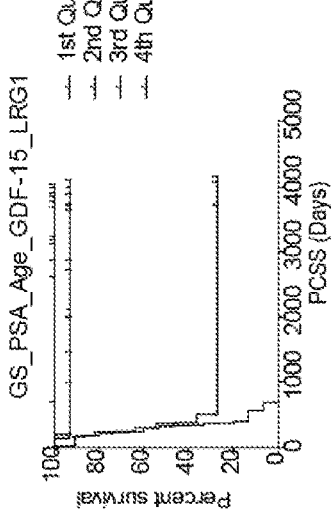
Figure 4C:
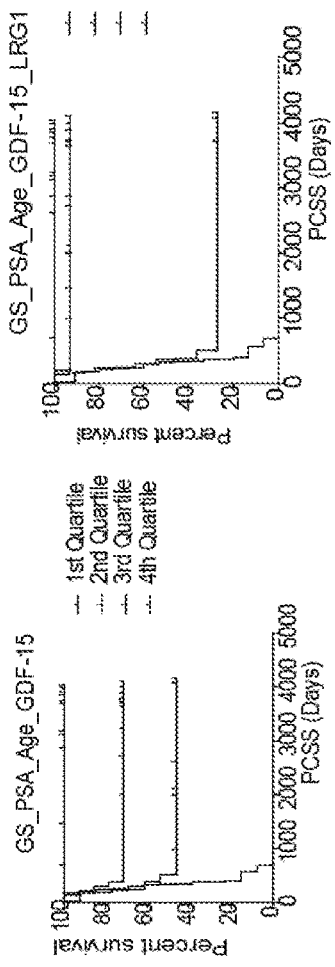

In this setting LRG1 on its own was a highly significant discriminator of high-grade, high-stage and more importantly fatal disease. Selection and implementation of an intermediate expression quartile based on the ELISA measurements allowed an accurate reclassification of a number of cases into high and low risk categories reinforcing the power of this marker in more accurate clinical decision-making (FIG. 2). LRG1 also enhanced the performance of PSA, age and Gleason grade in risk stratification when combined with these parameters (FIG. 3) and also enhanced the performance of a previously reported prognostic biomarker, GDF15 (also known as MIC-1), also a TGFbeta receptor superfamily ligand linked to angiogenesis and inflammation (FIG. 4).

This marker was next tested as a predictor of treatment response. Second-line therapies for recurrent disease typically deliver median survival benefits of around four months in clinical trials with little improvement on this median figure despite the recent introduction of new targeted agents such as Abiraterone (CYP17A1 inhibitor) and Enzalutamide (Androgen Receptor (AR) antagonist). These agents are administered because there is evidence that AR signalling remains active and significant at all stages of the disease. However some patients may obtain further benefits from combining these AR-targeted agents with other non-targeted therapies (radiation or chemotherapy). At present however clinicians have no basis on which to make that decision upfront. To assess the relevance of LRG1 for treatment decision-making blood samples were obtained from the SPCG-7 clinical trial at the Radium Hospital/ICR which compared the efficacy of androgen deprivation therapy alone versus a combination of radiotherapy and androgen deprivation therapy. It waa found that high levels of LRG1 correlated with a significantly better outcome in the treatment arm in which radiotherapy was combined with androgen deprivation therapy versus androgen deprivation therapy alone (Table 7). There was no significant difference in outcome between the treatment groups for patients with low levels of LRG1.

TABLE 1

| Study pipeline | | | |
|---|---|---|---|
| Aim | Method | Study cohort | Samples |
| Serum profiling | Mass spectrometry | Janus Serum Bank | 21 |
| Identify and rank candidates | Literature search | | |
| Validate MS data | Western blotting | | |
| Establish clinical assay | ELISA | | 61 |
| Define clinical implications | ELISA | STHLM2 | 764 |
| Benchmark against clinical standards | ELISA | CAPS | 200 |

TABLE 2

| | Baseline characteristics study cohorts | | | | | | | |
|---|---|---|---|---|---|---|---|---|
| | Janus | | STHLM2 | | CAPS | | | |
| | Controls | Cancer | Controls | Cancer | Control | Pre-diagnosis | Indolent | Aggressive |
| Age[+] | | | | | | | | |
| <65 | 31 | 22 | 179 | 136 | 24 | 19 | 0 | 22 |
| >65 | 0 | 8 | 194 | 254 | 26 | 31 | 50 | 28 |
| PSA (ng/ml)[+] | | | | | | | | |
| PSA <4 | | | 181 | 84 | 47 | 32 | 23 | 6 |
| PSA 4-19 | | | 189 | 264 | 0 | 18 | 27 | 9 |
| PSA >20 | | | 3 | 40 | 0 | 0 | 0 | 35 |
| Missing | 31 | 30 | 0 | 3 | 3 | 0 | 0 | 0 |
| Clinical T stage | | | | | | | | |
| T1 | | | 4 | 202 | | | 20 | 2 |
| T2 | | | 3 | 77 | | | 30 | 6 |
| T3 | | | 12 | 27 | | | 0 | 26 |
| T4 | | | 1 | 0 | | | 0 | 13 |
| Tx | | | 10 | 84 | | | 0 | 2 |
| Nodal metastases | | | | | | | | |
| N0 | | | | 48 | | | 0 | 1 |
| N1 | | | | 8 | | | 0 | 5 |
| Nx | | | | 334 | | | 0 | 44 |
| Distal metastases | | | | | | | | |
| M0 | | | 2 | 262 | | | 0 | 5 |
| M1 | | | 28 | 13 | | | 0 | 35 |
| Mx | | | | 115 | | | 0 | 10 |
| Biopsy Gleason Score | | | | | | | | |
| 2-6 | | | | 138 | | | 50 | 1 |
| 7 | | | | 116 | | | 0 | 6 |
| 8-10 | | | | 52 | | | 0 | 31 |
| Missing | | | 30 | 84 | | | 0 | 12 |

[+] at time of blood draw

TABLE 3

| ROC analysis of LRG1 with established risk factors for clinical status in STHLM cohort | | | | | | | | |
|---|---|---|---|---|---|---|---|---|
| | Status | | Established Risk Factors | | | Established Risk Factors + LRG1 | | |
| | Positive | Negative | | | | | | |
| Dependent | (n=) | (n=) | AUC | 95% CI | P_value | AUC | 95% CI | P_value |
| Cancer* | 296 | 373 | 0.711 | (0.672-0.750) | <0.0001 | 0.715 | (0.676-0.754) | <0.0001 |
| GS ≥8* | 51 | 617 | 0.800 | (0.728-0.871) | <0.0001 | 0.805 | (0.734-0.874) | <0.0001 |

TABLE 3-continued

ROC analysis of LRG1 with established risk factors for clinical status in STHLM cohort

| | Status | | Established Risk Factors | | | Established Risk Factors + LRG1 | | |
|---|---|---|---|---|---|---|---|---|
| Dependent | Positive (n=) | Negative (n=) | AUC | 95% CI | P_value | AUC | 95% CI | P_value |
| T stage ≥2c* | 25 | 644 | 0.903 | (9.848-0.957) | <0.0001 | 0.909 | (0.859-0.960) | <0.0001 |
| Metastasis§ | 18 | 278 | 0.845 | (0.763-0.926) | <0.0001 | 0.864 | (0.790-0.938) | <0.0001 |

*Established risk factors: PSA, Age
§Established risk factors: NICE categories

TABLE 4

ROC analysis of LRG1 with established risk factors for clinical status in CAPS cohort

| | Status | | Established Risk Factors | | | Established Risk Factors + LRG1 | | |
|---|---|---|---|---|---|---|---|---|
| Dependent | Positive (n=) | Negative (n=) | AUC | 95% CI | P_value | AUC | 95% CI | P_value |
| Cancer* | 87 | 98 | 0.904 | (0.861-0.947) | <0.0001 | 0.912 | (0.871-0.954) | <0.0001 |
| GS ≥8* | 31 | 154 | 0.919 | (0.867-0.980) | <0.0001 | 0.938 | (0.883-0.993) | <0.0001 |
| T stage ≥2c* | 30 | 155 | 0.911 | (0.844-0.979) | <0.0001 | 0.947 | (0.895-0.998) | <0.0001 |
| Metastasis§ | 26 | 13 | 0.846 | (0.688-1.000) | <0.0001 | 0.870 | (0.733-1.000) | <0.0001 |

*Established risk factors: PSA, Age
§Established risk factors: NICE categories

TABLE 5

Predictive value of LRG1 in a clinical model

| Risk of mortality | High | | Low | | | | | | | |
|---|---|---|---|---|---|---|---|---|---|---|
| Parameter | Dead | Alive | Dead | Alive | HR | Sensitivity | Specificity | PPV | NPV | LR |
| Clinical model* | 49 | 11 | 1 | 39 | 9.3 | 0.98 | 0.78 | 0.82 | 0.98 | 4.46 |
| Clinical model* + LRG1 | 50 | 4 | 0 | 46 | 18.2 | 1.00 | 0.92 | 0.93 | 1.00 | 12.50 |

*Clinical model = PSA, Age, T stage, Gleason Sum
HR = Hazard ratio
PPV = positive predictive value
NPV = Negative predictive value
LR = Likelihood ratio

TABLE 6

Pretreatment characteristics of eligible patients with determined LRG1

| Age, yrs | ≤Median (30 μg/mL) | | >Median (30 μg/mL) | | $X^2$ |
|---|---|---|---|---|---|
| <65 | 18 | 26.9 | 19 | 28.4 | |
| ≥65 | 16 | 23.9 | 14 | 20.9 | 0.70 |
| Median | 64.8 | | 64.4 | | |
| Range | (50.8-71.3) | | (49.6-73.4) | | |
| Gleason Score | | | | | |
| ≤7a | 23 | 34.3 | 21 | 31.3 | |
| >7a | 11 | 16.4 | 12 | 17.9 | 0.73 |
| PSA ng/mL | | | | | |
| <20 | 20 | 29.9 | 20 | 29.9 | |
| ≥20 | 14 | 20.9 | 13 | 19.4 | 0.88 |
| Median | 16.5 | | 16 | | |
| Range | (2.8-57.6) | | (3.3-69) | | |
| Tumor Stage | | | | | |
| ≤T2c | 9 | 13.4 | 4 | 6.0 | |
| >T2c | 25 | 37.3 | 29 | 43.3 | 0.14 |
| Assigned treatment | | | | | |
| ADT | 17 | 25.4 | 16 | 23.9 | |
| ADT + RT | 17 | 25.4 | 17 | 25.4 | 0.90 |

TABLE 7

Therapy response associated with pre-treatment plasma concentrations of LRG1 compared with PSA

| Treatment | LRG1 High | | LRG1 Low | | | PSA High | | PSA Low | | |
|---|---|---|---|---|---|---|---|---|---|---|
| | Dead | Alive | Dead | Alive | HR | Dead | Alive | Dead | Alive | HR |
| ADT | 7 | 9 | 2 | 15 | 3.94 | 3 | 8 | 6 | 16 | 0.93 |
| ADT + RT | 1 | 16 | 5 | 12 | 0.26 | 3 | 12 | 3 | 16 | 1.57 |

Example 2

This Example describes LRG1 as a biomarker of outcome after surgery and radiotherapy Most men who are diagnosed with PCa will have localized cancer. These men could be offered curative treatment such as surgery (radical prostatectomy, RP) or radiotherapy, although more than 20% have clinical relapse within 5 years. There are currently no blood-based biomarkers that can predict the outcome of RP as a treatment for localized prostate cancer. There is therefore a great need for more effective biomarkers for patient selection for different interventions and preferably biomarkers that are available by non-invasive measures.

Methods and Study Cohort Characteristics

Patient Samples

This retrospective study was based on 82 consecutive prostate cancer patients who had donated serum to Janus Serum Bank. The clinicopathological variables studied included age at sampling, preoperative prostate specific antigen (PSA) level, biopsy Gleason score, and prostate cancer specific mortality following treatment.

Statistical Analysis

Statistical analyses were performed in SPSS, v.22 (IBM, Chicago, Ill.). Patients were dichotomised based on median concentrations of LRG1 in serum in each treatment category. The impact of LRG1 levels on cumulative probability to encounter the clinical end-points (prostate cancer-specific survival) was assessed by Kaplan-Meier curves. Cox regression was used to establish independent predictors for prostate cancer specific survival.

Patient Cohort Baseline Characteristics

Comparing the baseline clinic-pathological features between the patients showing high concentrations of LRG1 in serum versus low levels in the surgery group there was no significant difference related to age, baseline PSA, Gleason score, tumor stage, metastasis to the lymph node, or distant metastasis (P=0.41, P=0.23, P=0.09, P=0.24, P=0.45 and 0.24 respectively) (Table 8). In the patient group that received radiation, there was a significant higher proportions of patients without know lymph node involvement in the group that had high LRG1 levels, but with no other significant association towards age, baseline PSA concentration, Gleason score, tumor stage, or distant metastasis (P=0.16, P=0.48, P=0.76, P=0.78, p=0.35 respectively). The general patient population in the radiation was more advanced prostate cancers than in the surgery group.

TABLE 8

Patient cohort baseline characteristic

| | Surgery | | | | Radiotherapy | | | |
|---|---|---|---|---|---|---|---|---|
| | n= | LRG1 low | LRG1 high | P | n= | LRG1 low | LRG1 high | P |
| Age, | | | | | | | | |
| median (yrs) | 32 | 59.1 | 61.1 | 0.41+ | 28 | 60 | 62.8 | 0.16+ |
| PSA | | | | | | | | |
| median (ng/mL) | 32 | 6.8 | 8.5 | 0.23+ | 28 | 11.3 | 18.1 | 0.48+ |
| Gleason score | | | | | | | | |
| ≤7a | 28 | 22 | 6 | | 13 | 8 | 5 | |
| ≥7b | 3 | 1 | 2 | | 10 | 4 | 6 | |
| Missing | 1 | 1 | 0 | 0.09* | 3 | 2 | 3 | 0.79* |
| T stage | | | | | | | | |
| T1-T2 | 16 | 13 | 3 | | 13 | 8 | 5 | |
| T3-T4 | 16 | 10 | 6 | | 12 | 5 | 7 | |
| Missing | 0 | 0 | 0 | 0.24* | 3 | 1 | 2 | 0.78* |
| N status | | | | | | | | |
| N0 | 10 | 8 | 2 | | 6 | 6 | 0 | |
| N1 | 0 | 0 | 0 | | 0 | 0 | 0 | |
| Nx | 21 | 14 | 7 | 0.45* | 18 | 6 | 12 | 0.007* |
| M status | | | | | | | | |
| M0 | 21 | 14 | 7 | | 11 | 7 | 4 | |
| M1 | 1 | 0 | 1 | | 5 | 2 | 3 | |
| Mx | 8 | 7 | 1 | 0.24* | 12 | 5 | 7 | 0.35* |

$P^+$ = Mann-Whitney,
$P^* = X^2$

Results

Surgery

Figure 5:
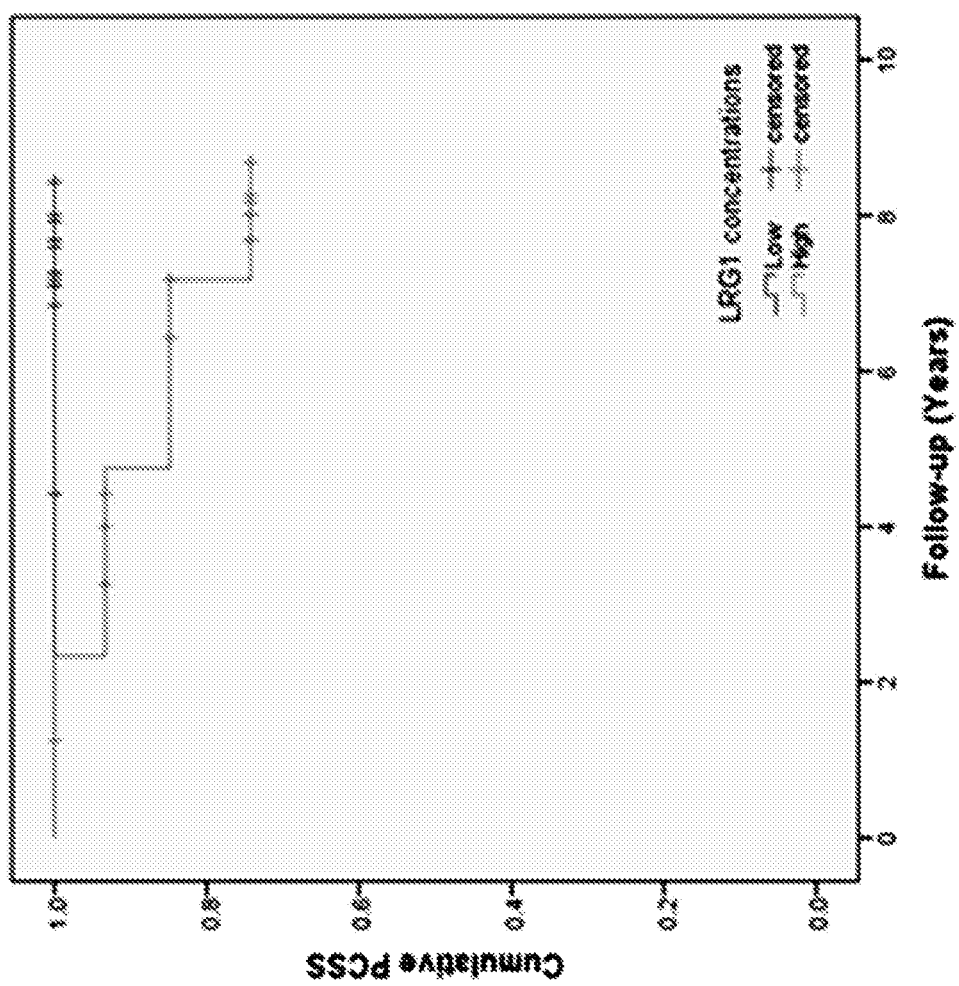
FIG. 5 shows a Kaplan Meier plot showing association of LRG1 with prostate cancer specific survival (PCSS) for patients undergoing surgery (RP).

In total 32 patients underwent surgery. The patients were dichotomized into two groups based on LRG1 serum concentrations (high versus low relative to median value). Three patients (9.4%) subsequently died of prostate cancer, all of whom were in the high LRG1 group (FIG. 5). The hazard ratio in the high LRG1 group was 8.4-fold higher than for the low LRG1 group (p=0.05). This indicates that LRG1 has utility for predicting outcome (risk of prostate-specific death) after surgery.

Radiotherapy

Figure 6:
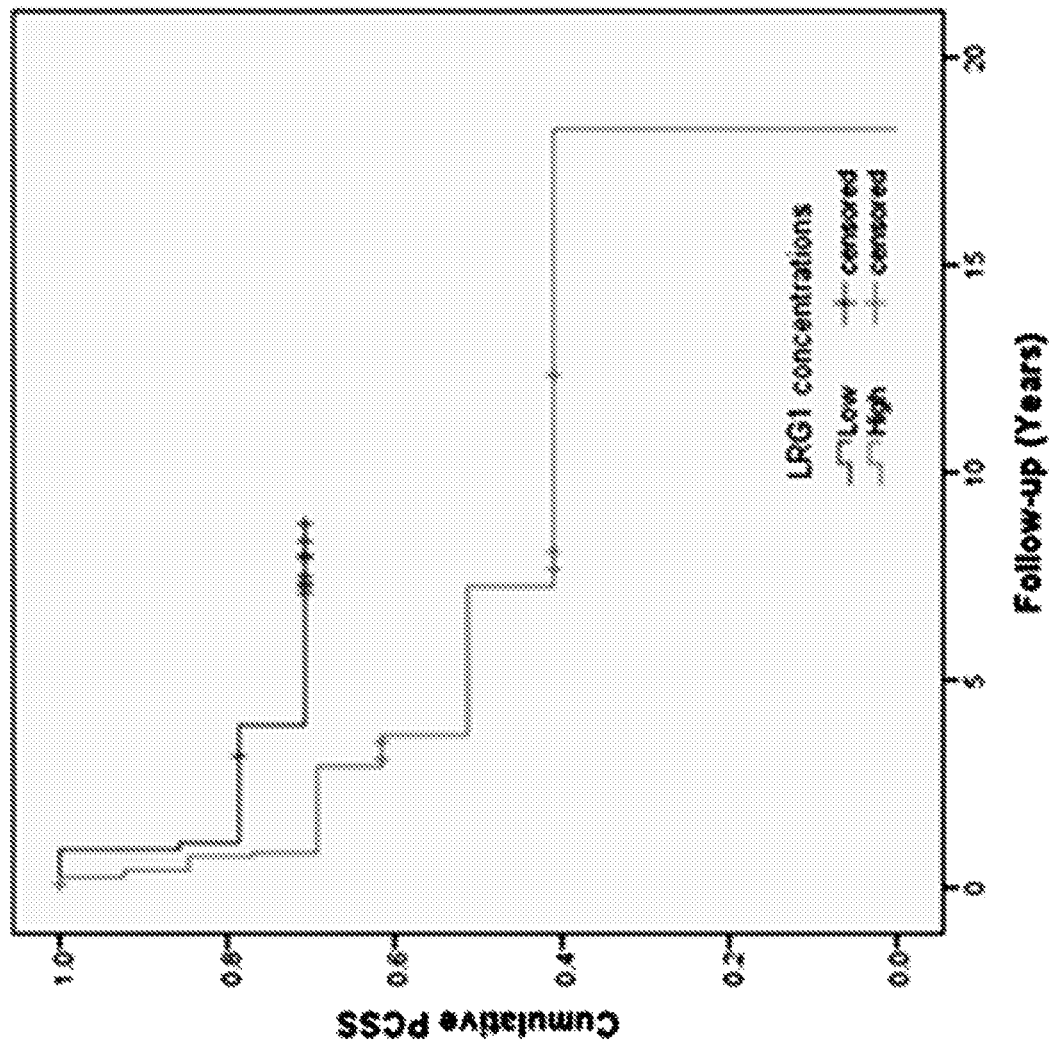
FIG. 6 shows a Kaplan Meier plot showing LRG1 association with prostate cancer specific survival (PCSS) for patients undergoing radiotherapy.

Twenty-eight patients underwent radiotherapy, and the patients were likewise dichotomized into two groups based on LRG1 serum concentrations (high versus low relative to median value). Twelve patients (43%) subsequently died of prostate cancer, 4 patients in the low LRG1 group, and 8 in the patient group that presented with LRG1 concentrations above median for this patient group (FIG. 6). Patients in the high LRG1 group had 2.47-fold higher risk (p=0.13) of having a prostate cancer specific mortality.

Furthermore, multivariate analysis by Cox regression showed that LRG1 is an independent predictor of poor outcome (p=0.005, Table 9), and a better predictor than PSA (p=0.068) in this setting. This demonstrates the utility of LRG1 for predicting outcome (risk of prostate-specific death) after radiotherapy.

In summary, the above data indicate that high pre-treatment LRG1 levels have utility in predicting outcome (e.g., risk of prostate-specific death) after both surgery and radiotherapy. In some embodiments, patients whose LRG1 levels indicate higher risk of prostate-specific death are offered more aggressive therapy, such as combination of radiotherapy and surgery, and radiotherapy in combination with adjuvant therapy, such as androgen deprivation therapy.

TABLE 9

Multivariate analysis for time to prostate cancer specific mortality

|  | HR | 95.0% CI | P= |
|---|---|---|---|
| LRG1 | 1.04 | (1.012-1.071) | .005 |
| Age | 0.93 | (0.821-1.045) | .212 |
| PSA ng/ml | 1.00 | (0.996-1.000) | .068 |
| Gleason Score | 2.55 | (1.077-6.041) | .033 |
| T stage | 3.01 | (0.783-11.571) | .109 |

Example 3

This Example describes LRG1 as a biomarker for improved stratification of locally advanced prostate cancer patients undergoing combined Androgen-Deprivation Therapy plus Radiotherapy Approximately 15% of patients with prostate cancer are diagnosed with "high-risk" disease, alternatively called "locally advanced" (Chang et al, Nat Rev Clin Oncol 2014, 11(6): p. 308-23). Patients with locally advanced PCa are routinely referred to treatments combining radiotherapy (RT) and androgen-deprivation therapy (ADT) with curative intent. Relapse is seen within 5 years in 20% of patients, and it is of high importance to predict which patients are likely to relapse.

This Example describes Leucine-rich alpha-2-glycoprotein 1 (LRG1) as a protein up-regulated in sera and plasma from PCa patients with aggressive phenotype. LRG1 is a 38 kDa protein that is highly expressed in liver and bone marrow (BM), and act as a part of the acute phase immune response by granulocytic differentiation and promotes angiogenesis, migration and cell adhesion (O'Donnell et al, J Leukocyte Biol 2002, 72(3):478-85; Kobe et al, Curr Opin Struct Biol 2001, 11(6):725-32; Takahashi et al, Proc Natl Acad Sci USA 1985, 82(7):1906-10; Saito et al, J Immunol 2002, 168(3):1050-9; Sun et al, Cancer Lett 1995, 89(1): 73-9; Cummings et al, Apoptosis 2006, 11(7):1121-9.

The primary site for metastasis in PCa is in bone marrow, and as LRG1 is highly expressed in bone marrow, it was investigated whether LRG1 levels in bone marrow have prognostic capacity even in PCa patients without distant metastasis detected and could aid the stratification of patients for prior to ADT and RT.

Study Cohorts and Methods

Training Cohort (SPCG-7)

During 1998-2005, 120 patients with locally advanced, lymph node negative PCa participated in the Oslo site for the "Scandinavian Prostate Cancer Group"-7 (SPCG-7) trial. From these, 75 were randomized into the trial arm with 3 months neo-adjuvant treatment of ADT followed by RT. Bone marrow (BM) plasma was available for all patients enrolled.

Test Cohort (IMRT)

Intensity-modulated radiotherapy (IMRT) is radiotherapy encompassing the prostate and pelvic lymph nodes. During 2004-2010, 43 patients with locally advanced PCa and lymph node negative were eligible for IMRT protocol after receiving 3-6 months with ADT. BM plasma was available from all 43 patients included in the trial.

ELISA Analysis

LRG1 levels in BM plasma were assessed by ELISA (IBL-America) as recommended by manufacturer.

Statistical Analysis

Statistical analyses were performed in SPSS, v.22 (IBM, Chicago, Ill.). LRG1 levels in BM plasma were dichotomised based on median values in BM plasma collected in the SPCG-7 cohort. The association between LRG1 BM-plasma levels and clinical and histopathological factors were analysed by Chi-square test (linear by linear association) for dichotomized variables. The impact of LRG1 BM-levels on cumulative probability to encounter the clinical end-points (overall survival and cancer-specific recurrence) was assessed by Kaplan-Meier curves, first in SPCG-7 and subsequently in IMRT.

Patient Cohort Baseline Characteristics

Comparing the baseline clinic-pathological features between the patients showing high concentrations of LRG1 in BM versus low levels in the training cohort (SPCG-7) there was no significant difference related to age, baseline PSA, Gleason score and tumor stage (P=0.69, P=0.57, P=0.30, P=0.69 respectively) (Table 10). In the test cohort (IMRT) LRG1 associated with higher age (P<0.0001), with no other significant association towards baseline PSA concentration, Gleason score and tumor stage (P=1.00, P=0.66, P=1.00, respectively).

TABLE 10

Patient cohort baseline characteristics

|  | Training cohort: SPCG-7 | | | | Test cohort: IMRT | | | |
|---|---|---|---|---|---|---|---|---|
|  | n= | LRG1 low | LRG1 high | P* | n= | LRG1 low | LRG1 high | P* |
| Age | | | | | | | | |
| <67 | 49 | 25 | 24 |  | 22 | 9 | 13 |  |
| ≥67 | 26 | 12 | 14 |  | 21 | 2 | 19 |  |
|  |  |  |  | 0.69 |  |  |  | 0.03 |
| PSA | | | | | | | | |
| <20 ng/ml | 43 | 20 | 23 |  | 12 | 3 | 9 |  |
| ≥20 ng/ml | 32 | 17 | 15 |  | 13 | 8 | 23 |  |
|  |  |  |  | 0.57 |  |  |  | 1.0 |

TABLE 10-continued

| | Patient cohort baseline characteristics | | | | | | | |
|---|---|---|---|---|---|---|---|---|
| | Training cohort: SPCG-7 | | | | Test cohort: IMRT | | | |
| | n= | LRG1 low | LRG1 high | P* | n= | LRG1 low | LRG1 high | P* |
| Gleason score | | | | | | | | |
| ≤7a | 47 | 21 | 26 | | 7 | 1 | 6 | |
| ≥7b | 28 | 16 | 12 | | 36 | 10 | 26 | |
| | | | | 0.30 | | | | 0.66 |
| T stage | | | | | | | | |
| T1-T2 | 9 | 5 | 4 | | 10 | 2 | 8 | |
| T3-T4 | 66 | 32 | 34 | | 33 | 9 | 24 | |
| | | | | 0.69 | | | | 1.0 |

$P^* = X^2$

Results

Concentrations of LRG1 were measured in bone marrow plasma collected from patients with locally advanced prostate cancer receiving androgen-deprivation therapy in combination with radiotherapy from two cohorts, SPCG-7 (training cohort) and IMRT (test cohort). The median measurable level of LRG1 in bone marrow plasma in the training cohort was used to set a prediction threshold, which was subsequently applied to samples similarly measured in the test cohort (IMRT).

Figure 7B:
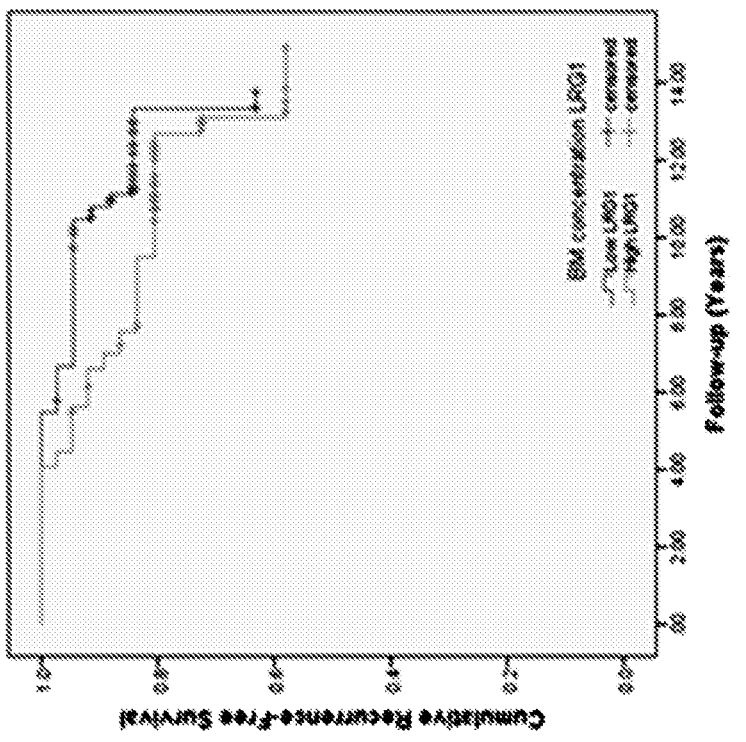
FIG. 7A-B shows Kaplan-Meier plots showing association of LRG1 with biochemical recurrence-free survival in training (A) and test (B) cohorts.
Figure 7A:
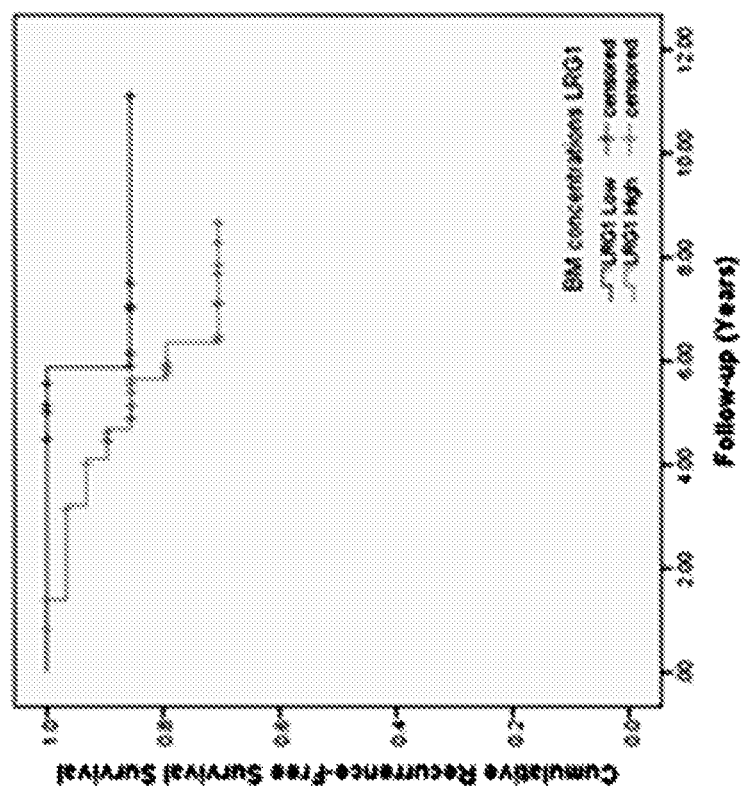
Figure 8A:
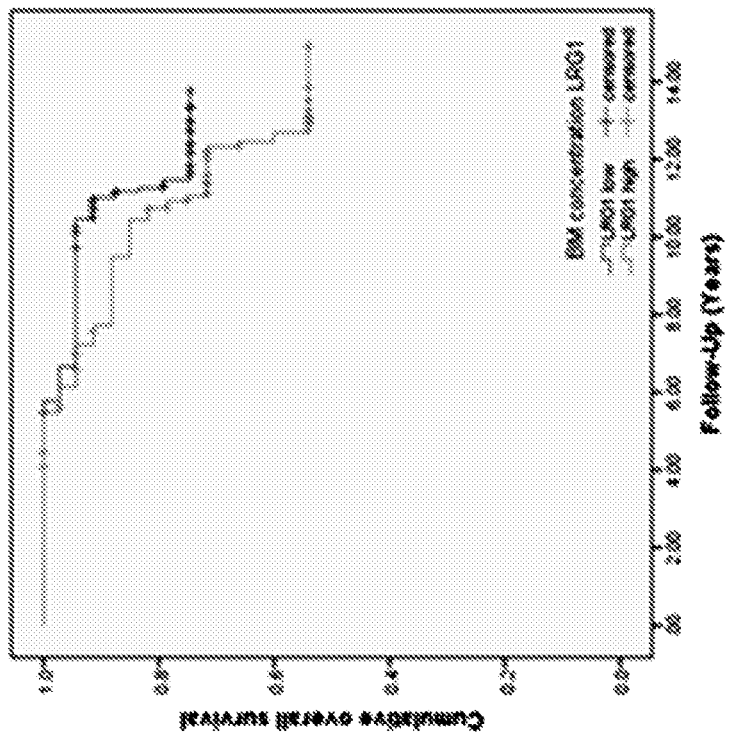
FIG. 8A-B shows Kaplan-Meier plots showing association of LRG1 with overall survival rate in training (A) and test (B) cohorts.
Figure 8B:
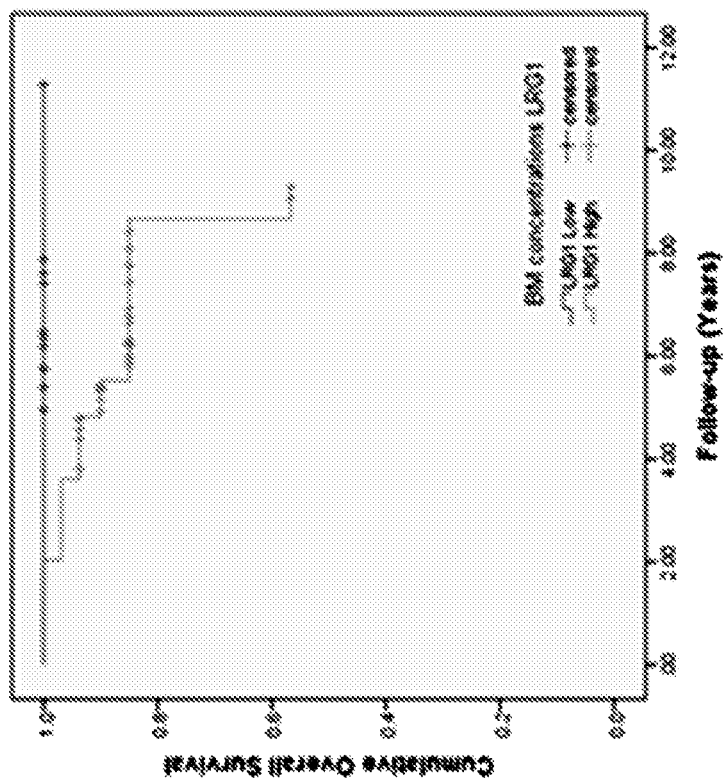

From the total of 75 patients following ADT and radiotherapy in the training cohort, 15 (22.7%) patients had biochemical recurrence within 14 years. After having stratified patients based on their concentration of LRG1 in BM plasma, patients with above median (high) LRG1 concentration showed a 1.4 fold increased risk of having biochemical failure, 23% (9/38) vs 16% (6/37) in the low LRG1 group (FIG. 7A). This was further tested in an independent cohort, IMRT, of 43 patients. In this cohort, higher LRG1 concentrations in bone marrow indicated 2.3 higher risk of having biochemical recurrence within 12 years of treatment. Recurrence frequency was 9% (1/11) in the low LRG1 group vs 19% (6/32) in the high LRG1 group (FIG. 7B). The predictive value of LRG1 in bone marrow was further evaluated with survival as outcome measure, demonstrating the same trend as for biochemical recurrence (FIG. 8). In the training cohort, the high LRG1 group had 12 deaths among 38 patients (32%), compared to 7 deaths among 37 patients (19%) in the low LRG1 group. Similarly, all 5 deaths in the IMRT cohort were in the high LRG1 group (5/32 vs 0/12). Taken together, the above data indicate that LRG1 levels in bone marrow are predictive of outcome after combination therapy with ADT and RT, with respect to both biochemical recurrence and survival.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method for treating a subject diagnosed with prostate cancer, comprising:
   (a) determining the level of LRG1 polypeptide in a blood sample from the subject with an immunoassay using an immunoglobulin specific for said LRG1 polypeptide;
   (b) classifying said subjects as being at an increased risk of prostate cancer-specific death by comparing the level of said LRG1 polypeptide to a reference level of LRG1 polypeptide in a relevant control subject or group of subjects, wherein elevated levels of said LRG1 polypeptide in the blood sample as compared to said reference level is indicative of an increased risk of prostate cancer-specific death of a subject diagnosed with prostate cancer; and
   (c) treating said subjects classified as having an increased risk of prostate cancer-specific death in step (b) with adjuvant treatment comprising radiotherapy and androgen deprivation therapy.

2. The method of claim 1, wherein said adjuvant treatment further comprising surgery.

3. The method of claim 1, further comprising the step of detecting the presence, absence, or level of one or more additional markers.

4. The method of claim 3, wherein said markers are PSA and/or Growth Differentiation Factor 15.

5. A method for determining treatment for a subject diagnosed with prostate cancer, comprising:
   (a) determining the level of LRG1 polypeptide in a blood sample from the subject with an immunoassay using an immunoglobulin specific for said LRG1 polypeptide;
   (b) classifying said subject as being at an increased risk of prostate cancer-specific death by comparing the level of said LRG1 polypeptide to a reference level of LRG1 polypeptide in a relevant control subject or group of subjects, wherein elevated levels of said LRG1 polypeptide in the blood sample as compared to said reference level is indicative of an increased risk of prostate cancer-specific death; and
   (c) treating said subjects classified as having an increased risk of prostate cancer-specific death in step (b) with adjuvant treatment, wherein said adjuvant treatment is selected from the group consisting of treatment by radiotherapy and androgen deprivation therapy, and treatment by surgery, radiotherapy and androgen deprivation therapy.

6. The method of claim 5, wherein said adjuvant treatment is treatment by radiotherapy and androgen deprivation therapy.

7. The method of claim 5, wherein said adjuvant treatment is treatment by surgery, radiotherapy and androgen deprivation therapy.

8. The method of claim 5, further comprising the step of detecting the presence, absence, or level of one or more additional markers.

9. The method of claim 8, wherein said markers are PSA and/or Growth Differentiation Factor 15.

* * * * *